(12) United States Patent
Hodge et al.

(10) Patent No.: US 7,629,167 B2
(45) Date of Patent: Dec. 8, 2009

(54) DISPOSABLE BIOREACTOR SYSTEMS AND METHODS

(75) Inventors: Geoffrey Hodge, Sutton, MA (US);
Parrish Galliher, Littleton, MA (US);
Michael Fisher, Ashland, MA (US)

(73) Assignee: XCELLEREX, Inc., Marlborough, MA (US)

(*) Notice: Subject to any disclaimer, the term of this patent is extended or adjusted under 35 U.S.C. 154(b) by 596 days.

(21) Appl. No.: 11/147,124

(22) Filed: Jun. 6, 2005

(65) Prior Publication Data

US 2005/0272146 A1    Dec. 8, 2005

Related U.S. Application Data

(60) Provisional application No. 60/577,143, filed on Jun. 4, 2004, provisional application No. 60/669,252, filed on Apr. 7, 2005.

(51) Int. Cl.
*C12M 1/00* (2006.01)
*C12M 3/00* (2006.01)
*C12M 1/02* (2006.01)
*B01F 13/08* (2006.01)

(52) U.S. Cl. ............... 435/289.1; 435/290.2; 435/296.1; 435/302.1; 366/274

(58) Field of Classification Search ............... 435/289.1, 435/290.2, 296.1, 302.1; 261/121.1, 122.1; 366/273, 274, 102, 103, 104
See application file for complete search history.

(56) References Cited

U.S. PATENT DOCUMENTS

| | | | | |
|---|---|---|---|---|
| 2,793,166 A | * | 5/1957 | Hatch | 435/289.1 |
| 2,956,739 A | * | 10/1960 | Tothill | 416/137 |
| 2,958,517 A | * | 11/1960 | De Long et al. | 435/302.1 |
| 4,080,663 A | | 3/1978 | Wik | 366/274 |
| 4,162,855 A | * | 7/1979 | Bender | 366/274 |
| 4,620,794 A | | 11/1986 | Leka | 366/131 |
| 4,671,667 A | | 6/1987 | Augustin | 366/279 |
| 4,725,149 A | | 2/1988 | Kawakami et al. | 366/141 |
| 4,808,348 A | | 2/1989 | Rudick et al. | 261/82 |
| 4,830,511 A | | 5/1989 | Smazik | 366/273 |
| 4,877,522 A | | 10/1989 | Toei et al. | 210/198.2 |

(Continued)

FOREIGN PATENT DOCUMENTS

CA    2 271 583 C    4/2002

(Continued)

OTHER PUBLICATIONS

U.S. Appl. No. 11/064,252, filed Feb. 22, 2005, Kunas et al.

*Primary Examiner*—William H Beisner
*Assistant Examiner*—Danielle Henkel
(74) *Attorney, Agent, or Firm*—Jacqueline Arendt

(57) ABSTRACT

Accordingly, in one embodiment of the invention, a bioreactor system is presented and includes a disposable container for housing biomaterials for processing, the disposable container including at least one input port, at least one exhaust port, at least one harvest port, and the integrity of the sterile environment is protected with sterile filters attached to all external open ports a structure for supporting the disposable container, one or more sensors for sensing one or more parameters of the biomaterials in the container, a heater for heating the contents of the container, the heater having a thermostat and mixing system arranged with the system such that biomaterials contained in the disposable container are mixed.

27 Claims, 7 Drawing Sheets

U.S. PATENT DOCUMENTS

| | | | |
|---|---|---|---|
| 4,882,062 A | 11/1989 | Moeller et al. | 210/656 |
| 5,028,142 A | 7/1991 | Ostoich et al. | 366/273 |
| 5,040,898 A | 8/1991 | Sweatman et al. | 366/273 |
| 5,075,234 A * | 12/1991 | Tunac | 435/301.1 |
| 5,081,035 A * | 1/1992 | Halberstadt et al. | 435/297.4 |
| 5,156,701 A | 10/1992 | Spencer et al. | |
| 5,183,336 A * | 2/1993 | Poltorak et al. | 366/273 |
| 5,205,783 A | 4/1993 | Dieckert et al. | 454/238 |
| 5,227,138 A | 7/1993 | Boyd et al. | 422/102 |
| 5,240,322 A | 8/1993 | Haber et al. | 366/130 |
| 5,249,957 A | 10/1993 | Hirata | 431/354 |
| 5,261,742 A | 11/1993 | Lockhart | 366/141 |
| 5,342,781 A | 8/1994 | Su | |
| 5,352,036 A | 10/1994 | Haber et al. | 366/130 |
| 5,401,212 A | 3/1995 | Marvell et al. | 454/187 |
| 5,427,450 A | 6/1995 | Gambrill | 366/168 |
| 5,478,149 A | 12/1995 | Quigg | 366/273 |
| 5,578,201 A | 11/1996 | Collier et al. | 210/142 |
| 5,591,344 A | 1/1997 | Kenley et al. | 210/636 |
| 5,656,491 A | 8/1997 | Cassani et al. | 435/283.1 |
| 5,664,938 A | 9/1997 | Yang | 417/313 |
| 5,758,965 A | 6/1998 | Gambrill et al. | 366/273 |
| 5,779,359 A | 7/1998 | Gambrill et al. | 366/273 |
| 5,918,093 A | 6/1999 | Kim | 399/237 |
| 5,939,313 A * | 8/1999 | Cheng | 435/289.1 |
| 5,985,535 A | 11/1999 | Urabe | 430/569 |
| 6,086,243 A | 7/2000 | Paul et al. | 366/273 |
| 6,231,760 B1 | 5/2001 | Siddiqi | 210/222 |
| 6,247,840 B1 | 6/2001 | Gaffar | 366/274 |
| 6,357,907 B1 | 3/2002 | Cleveland et al. | 366/273 |
| 6,379,625 B1 | 4/2002 | Zuk, Jr. | 422/101 |
| 6,391,698 B1 | 5/2002 | Tung | |
| 6,402,367 B1 | 6/2002 | Lu et al. | 366/273 |
| 6,416,215 B1 | 7/2002 | Terentiev | 366/273 |
| 6,432,698 B1 | 8/2002 | Gaugler et al. | 435/296.1 |
| 6,467,946 B1 | 10/2002 | Gebrian | 366/273 |
| 6,500,343 B2 | 12/2002 | Siddiqi | 210/695 |
| 6,514,137 B1 | 2/2003 | Panellie et al. | 454/187 |
| 6,544,788 B2 | 4/2003 | Singh | 435/383 |
| 6,555,011 B1 | 4/2003 | Tribelsky et al. | 210/748 |
| 6,637,927 B2 | 10/2003 | Lu et al. | 366/273 |
| 6,670,171 B2 * | 12/2003 | Carll | 435/289.1 |
| 6,673,598 B1 | 1/2004 | Akers et al. | |
| 6,709,862 B2 | 3/2004 | Curtis | |
| 6,736,906 B2 | 5/2004 | Cotte et al. | 134/33 |
| 6,758,593 B1 | 7/2004 | Terentiev | 366/273 |
| 6,764,859 B1 | 7/2004 | Kreuwel et al. | 436/178 |
| 6,837,613 B2 | 1/2005 | Terentiev | 366/273 |
| 7,357,567 B2 | 4/2008 | Terentiev | 366/273 |
| 7,384,027 B2 | 6/2008 | Terentiev et al. | 261/93 |
| 7,384,783 B2 | 6/2008 | Kunas et al. | 435/289.1 |
| 2002/0110915 A1 * | 8/2002 | Shaaltiel | 435/393 |
| 2003/0008389 A1 | 1/2003 | Carll | 435/302.1 |
| 2003/0036192 A1 | 2/2003 | Singh | 435/297.2 |
| 2003/0170810 A1 | 9/2003 | Vedadi et al. | 435/69.1 |
| 2003/0198128 A1 | 10/2003 | Carlson | 366/331 |
| 2004/0062140 A1 | 4/2004 | Cadogan et al. | 366/144 |
| 2004/0203140 A1 | 10/2004 | Akers et al. | |
| 2004/0218468 A1 | 11/2004 | Terentiev | 366/273 |
| 2004/0229335 A1 | 11/2004 | Zhang et al. | 435/235.1 |
| 2005/0002274 A1 | 1/2005 | Terentiev | 366/274 |
| 2005/0002275 A1 | 1/2005 | Gigas et al. | 366/273 |
| 2005/0058632 A1 | 3/2005 | Hedrick et al. | |
| 2005/0076076 A1 | 4/2005 | Galbraith | 709/200 |
| 2005/0239199 A1 * | 10/2005 | Kunas et al. | 435/297.1 |

FOREIGN PATENT DOCUMENTS

| | | |
|---|---|---|
| DE | 0 200 792 | 2/1985 |
| DE | 199 17 398 A1 | 10/2000 |
| FR | 2 799 138 | 10/1999 |
| GB | 2 202 549 A | 9/1988 |
| JP | 60164476 A * | 8/1985 |
| JP | 9-141079 | 12/1998 |
| WO | WO 98/52629 | 11/1998 |
| WO | WO 2005/068059 * | 7/2005 |

* cited by examiner

DISPOSABLE BIOREACTOR SYSTEMS AND METHODS

CLAIM TO PRIORITY AND RELATED APPLICATIONS

This applications claims the benefit of U.S. provisional patent application No. 60/577,143, filed Jun. 4, 2004 (Jun. 4, 2005 being a Saturday), entitled, "DISPOSABLE BIOREACTOR", and U.S. provisional patent application No. 60/669,252, filed Apr. 7, 2005, entitled, "MIXING SYSTEM PATENT APPLICATION", both disclosures of which, in their entirety are herein incorporated by reference. The current application is also related to co-pending U.S. patent application Ser. No. 11/050,133, filed Feb. 3, 2005, the entire disclosure of which is herein incorporated by reference.

FIELD OF THE INVENTION

Embodiments of the present invention are directed to methods and systems for processing biological materials, and more particularly, to disposable components/systems for processing biological materials.

BACKGROUND

Traditional bioreactors are designed as stationary pressurized vessels which can be mixed by several alternative means, while current disposable bioreactors are devices which utilize plastic sterile bag. Each is used to process biological materials (for example, to grow plant, animal cells) Including, for example, mammalian, plant or insect cells and microbial cultures/Such devices may also be used for sterile mixing as well as non-sterile mixing applications.

Mixing has been accomplished in the pressurized vessels using impeller devices, while in disposable systems, it has been accomplished by rocking of the container the bioreactor back and forth. For example, as shown in U.S. Pat. No. 6,544,788, to Singh, a disposable bioreactor is disclosed which accomplishes mixing by such a back and forth motion/process. This process is limited and cannot be utilized in a quick and efficient manner. Specifically, the rocking motion is limited to a low number of back and forth movements so as not to stress the bag and system.

Moreover, current disposable bioreactors do not include a total disposable system—probes, sensors and other components are generally used again and required sterilization prior to repeated use. Thus, current state of the art disposable bioreactor systems are not efficient, especially when it comes to mixing, and have a lag time between uses so that probes, sensors and/or other components may be sterilized prior to another use.

What is needed is a cost effective disposable bioreactor system in which many components are disposable and one which limits downtime between uses, and/or one which includes an improved mixing system.

SUMMARY OF THE INVENTION

Accordingly, embodiments of the present invention address the drawbacks and shortcomings of the prior art bioreactor systems and present an improved disposable bioreactor system. In particular, embodiments of the present invention provide mixing, aeration and/or process control, to which a substantial number (e.g., most) of the typical utilities required to run a bioreactor have been eliminated.

To that end, some embodiments of the present invention include a bioreactor system based on a disposable bioprocess bag in which the sterile envelope defined by the interior of the disposable bioreactor bag includes disposable components of a mixing system which do not require the need for rocking the envelope or the use of a peristaltic pump on tubing external to the bag. Moreover, some embodiments of the present invention provide a total disposable solution—all contact surfaces, including probes and sensor may be disposable.

These and other embodiments of the invention include the advantage of decreasing wear and tear on the sterile envelope provided by the disposable bioreactor, thus reducing the chance of a breach of the sterile envelope due to mechanical stress. The embodiments of the invention which do not require the rocking moving mixing also include advantages in non-sterile applications in which the integrity of the disposable plastic container is important.

Accordingly, in one embodiment of the invention, a bioreactor system is presented and includes a disposable container for housing biomaterials for processing, the disposable container including at least one input port, at least one exhaust port, at least one harvest port, a structure for supporting the disposable container, one or more sensors for sensing one or more parameters of the biomaterials in the container, a heater for heating the contents of the container, the heater having a thermostat and mixing system arranged with the system such that biomaterials contained in the disposable container are mixed.

In another embodiment of the invention, a bioreactor system is provided and may include at least one and preferably all of a support structure and a flexible plastic bag positioned within the support structure. The disposable container may include an impeller plate affixed to a lower portion of the flexible plastic bag, where the impeller plate may include a post. The disposable container may also include an impeller hub mounted on the post, the impeller hub having at least one impeller blade arranged on the post and having at least one magnet. The bioreactor system may further include a motor having shaft, the motor being provided adjacent to or within the support structure and a motor hub mounted on the motor shaft. The motor hub may include at least one magnet, where upon mounting of the flexible plastic bag within the support structure, the motor hub aligns with the impeller plate such that the magnet of the motor hub may align with the magnet of the impeller hub to drive the impeller hub when the motor shaft rotates.

In yet another embodiment of the invention includes a bioreactor system which may include a support structure and a flexible plastic bag positioned within the support structure. The disposable container may include an impeller plate affixed to a lower portion of the flexible plastic bag, a first shaft having a first end positioned within the interior of the flexible plastic bag and having a second end positioned on an exterior of the flexible plastic bag, a seal surrounding the shaft and an impeller hub mounted on the first end of the shaft, the impeller hub having at least one impeller blade arranged on the shaft. The bioreactor system may also include a motor arranged adjacent to or within the support structure, upon mounting of the flexible plastic bag within the support structure, the second end of the shaft is driven by the motor.

These and other objects, advantages and features of the invention will become even more apparent with reference to the following detailed description and attached drawings, a brief description of which is provided below.

DETAILED DESCRIPTION OF THE INVENTION

A bioprocess container forms the product contact surface for the bioreactor. The container is preferable a flexible bag which may be placed in a rigid structure such as a tank shell for support. The support structure may also include/involve a movable dolly, so that the bioreactor system may be moved to different locations before, during and after material processing.

Fittings are added to the bag to enable functionality required in a bioreactor such as penetrations and filters to allow for fluid and gas transfer, a mixing interface, sensors and a sparing surface to control bubble size. For application as a bioreactor, the vessel (the core bioprocess bag plus all attachments, penetrations, sensors, etc.) may be sterilized prior to use (e.g., gamma-irradiation). After sterilization, the inside of the bag, tubing and components may be considered sterile, providing a "sterile envelope" protecting the contents of the vessel from airborne contaminants outside. Bubble size and distribution can be controlled by passing the inlet gas stream through a porous surface prior to addition to the interior of the disposable bioreactor. Moreover, the sparging surface may be used as a cell separation device by alternating pressurization and depressurization (or application of vacuum) on the exterior surface of the porous surface, for example, or by a Bernoulli effect created by fast flow along one portion of the porous surface causing depressurization along other parts of the surface (e.g. fast flowing air in the center of a tube, exiting at one end of the tube, creating a vacuum along the length of the tube).

Figure 1A:
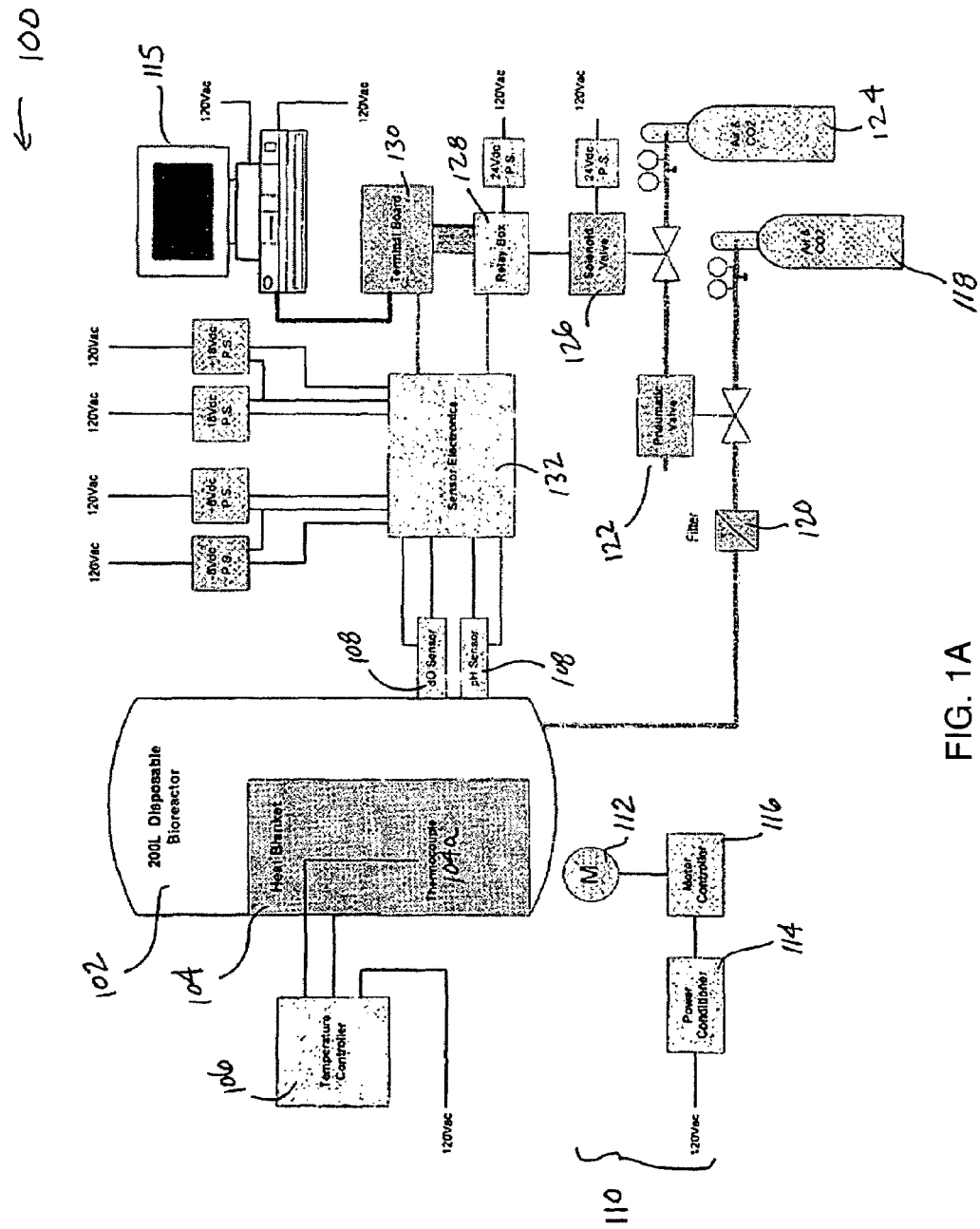
FIG. 1A is a block diagram of an overview of a bioreactor system according to one embodiment of the present invention.
Figure 1B:
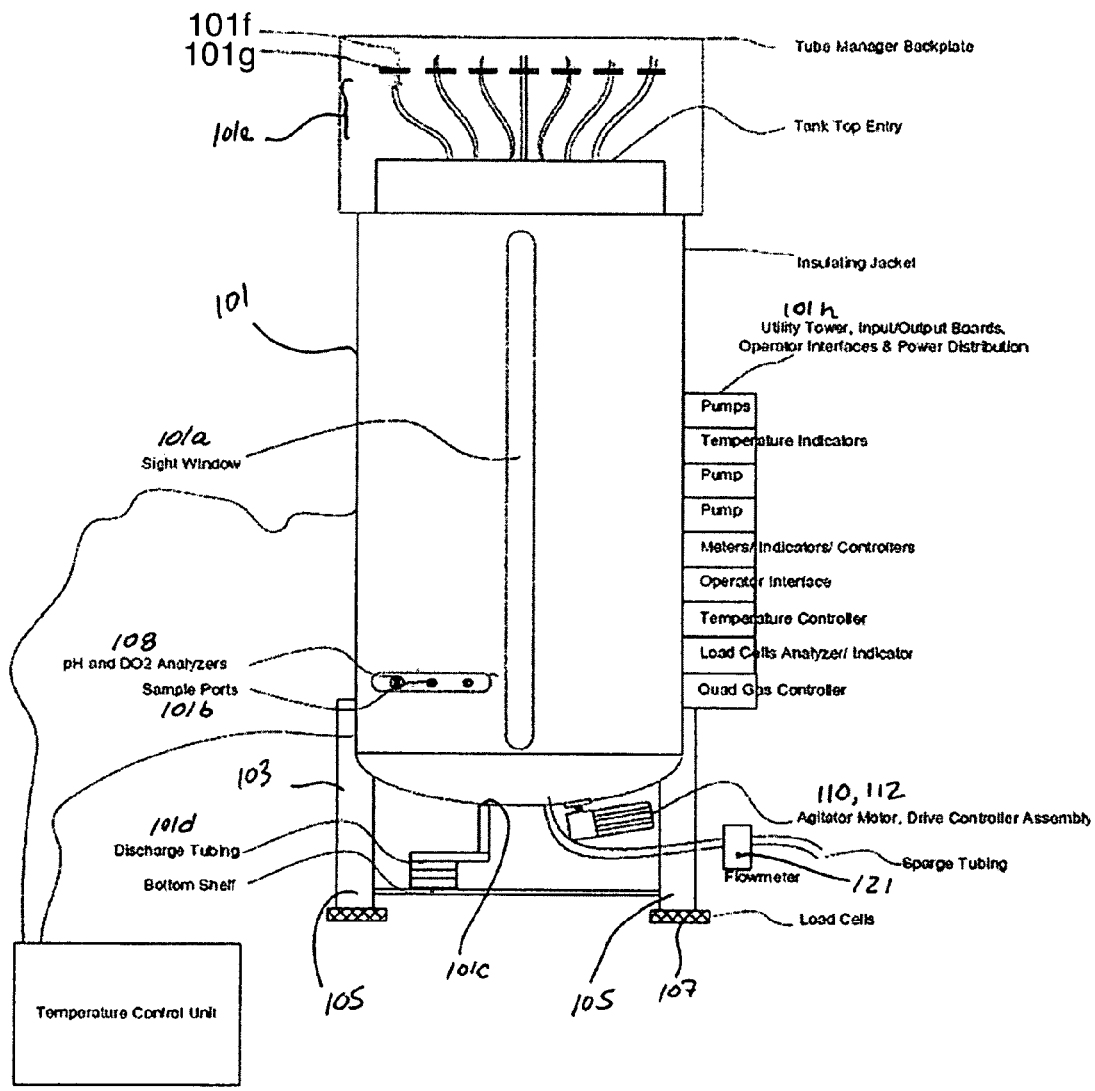
FIG. 1B is a schematic diagram of a bioreactor system according to an embodiment of the present invention.

As shown in FIGS. 1A and 1B, a bioreactor system 100 may include one or more of the following: a disposable bioreactor 102, a temperature controller 106 and one or more sensor and/or probes 108. To eliminate utilities required for temperature control through a heat exchanger, heating can be provided by means of closed loop water jacket heated and/or cooled by control system mounted on the bioreactor or by an electric heating blanket(s) 104, or Peltier heaters. The heat blanket may include a thermocouple(s) 104a for sensing a temperature of the contents of the bioreactor 102, working in conjunction with the temperature controller to control a set temperature of the contents of the bioreactor 102. A temperature conducting material may be embedded in the surface of the bag to overcome the insulating effect of plastic if necessary.

In some embodiments of the invention, the disposable bioreactor may comprise a plastic, flexible bag, but may also comprise a rigid material (e.g., plastic, metal, glass). The sensors and/or probes typically are connected to sensor electronics 132, the output of which is sent to either or both of the terminal board and relay. A mixing system 110, which generally includes a motor 112 for driving an impeller positioned in the bioreactor, a power conditioner 114 and motor controller 116, may also be provided.

Cooling may also be provided by a closed loop water jacket heated and/or cooled by control system mounted on the bioreactor or by standard heat exchange through a cover/jacket on the tank (the heat blanket may be included in a device for both heating/cooling but may also be separate from a cooling jacket). Cooling may also be provided by means of Peltier coolers. For example, a Peltier cooler may be applied to an exhaust line (e.g., to a chamber similar to a small bag, with a large volume to decelerate air and a large surface area) to condense gas in the exhaust air to help prevent an exhaust filter from wetting out.

Air, oxygen and/or $CO_2$ gas (compressed or pumped) 118 may be included so as to provide sparging to the contents of the bioreactor. A filter 120, a flowmeter 121, and/or valve 122 (e.g., pneumatic) may be provided in-line, the latter of which may be controlled by a controller system 115, which, as illustrated, may be a PC. Such a controller system may include a combination of electronic, mechanical or pneumatic systems to control air, liquid and heat to the disposable bioreactor system. As shown in FIG. 1, valve 122 may be a pneumatic actuator (using, e.g., compressed air/$CO_2$ 124 which may be controlled by a solenoid valve 126. The solenoid valve in turn may be controlled by a relay 128 connected to a terminal board 130 which is connected to the PC. The terminal board may comprise a PCI terminal board, or a USB/parallel, or fireport (IEEE 394) terminal board connection.

Figure 8A:
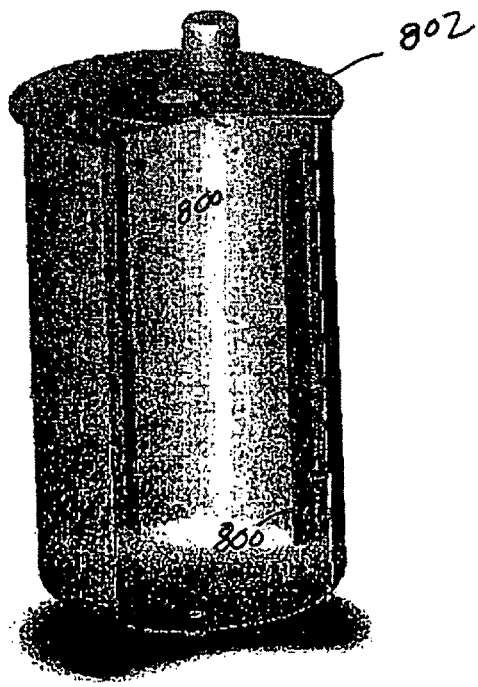
FIG. 8A is a perspective illustration of a support structure/tank having one or more baffles—the disposable bioreactor bag placed into such a tank conforms to the baffles.
Figure 8B:
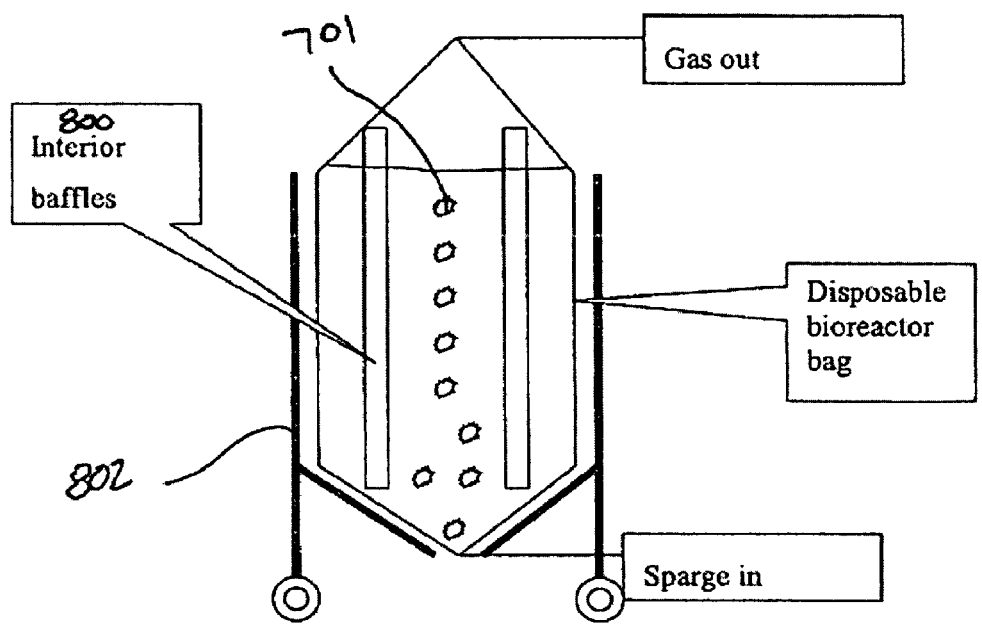
FIG. 8B is a schematic diagram illustrating an embodiment of the present invention which includes a bubble/air-lift mixing system (FIG. 7) and interior baffles in the support structure (FIG. 8A).

As shown in FIG. 1B, the disposable bioreactor preferably is supported by a support structure 101, which is shown as a tank (e.g., stainless steel), mounted atop a base 103, having a plurality of legs 105. The tank may be designed to include a height and diameter similar to standard stainless steel bioreactors. The design may also be scaleable down to small bench bioreactor volumes and up in excess of 1000 L working volumes (for example). Baffles 800 (see FIGS. 8A and 8B) may be built into the interior of the hard tank shell 802 to improve mixing by causing the bag to conform a shape that protrudes into the bioreactor bag, which preferably breaks up circular flow and/or prevents vortexing (for example).

Under at least one of the legs (preferably all the legs) may be a load cell 107, which may be used to estimate the weight of the contents of the bioreactor, and/or the tank and corresponding components of the tank. The tank may include a sight window 101a, which allows one to view a fluid level within the disposable bioreactor. The sight window may also be sized to allow one to see a large area of the bioreactor. The tank may also include sensor/probe ports 101b, an outlet 101c, to which discharge tubing 101d may be connected. At a top portion of the tank, one or more connections (e.g., tubes, valves, openings) 101e, for fluids, gases, and the like, to be added or withdrawn (e.g., intakes/exhausts) from the bioreactor, each of which may include a flow sensor 101*f* and/or filter 101*g*. A utility tower 101*h* may be provided on or adjacent the tank, which may be used to house one or more pumps, controllers and electronics (e.g., the sensor electronics, electronics interfaces, pressurized gas controller, etc.).

Sensors/probes and controls for monitor and controlling important process parameters include any one or more, and combinations of: temperature, pressure, pH, dissolved oxygen (DO), dissolved carbon dioxide ($pCO_2$), mixing rate, and gas flow rate (for example). Preferably process control may be achieved in ways which do not compromise the sterile barrier established by the bioreactor. In particular, gas flow may be monitored and/or controlled by a rotameter or a mass flow meter upstream of an inlet air filter.

Disposable optical probes may be designed to use "patches" of material containing an indicator dye which can be mounted on the inner surface of the disposable bioreactor bag and read through the wall of the bag via a window in the tank. For example, dissolved oxygen (DO) and/or pH and or $CO_2$ each may be monitored and controlled by an optical patch and sensor mounted on a, gamma-irradiatable, biocompatabile polymer which, in turn sealed to, embedded in, or otherwise attached to the surface of the bag.

Pressure may be monitored and controlled by standard pressure transducers upstream of an inlet air filter and downstream of an exhaust air filter. Alternatively disposable pressure sensors can be used inside the sterile envelope of the disposable bioreactor, either by taking off the shelf devices (e.g. Utah Medical or Honeywell) or by creating a tee on the air inlet and/or exhaust line. The surface of the tee can also be covered with a membrane to maintain the sterile barrier, but manufactured so as to not impact pressure readings. A standard pressure transducer may then be fitted to the tee to measure and control pressure inside the sterile barrier.

Figure 2:
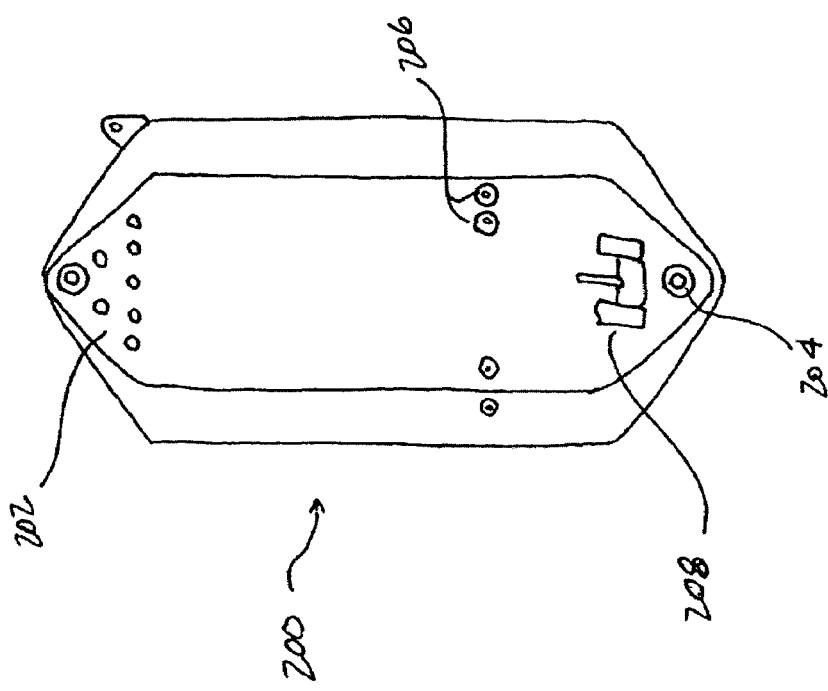
FIG. 2 is a schematic diagram of a disposable bioreactor bag according to an embodiment of the present invention.

FIG. 2 illustrates an example of the disposable bioreactor 200 according to some embodiments of the invention. As shown, the bioreactor includes one or more ports 202 which may be used to add or withdraw gases and/or fluids from the bioreactor. A harvest or drainage port 204 is generally provided at the bottom of the bag so that gravity may be used to direct the contents out of the bioreactor. The probes and/or sensors 206 may be integral with a side of the bioreactor, such that the sensors and/or probes may be disposable as well. In one embodiment of the invention, the sensors/probes may be optical probes which present the output in a visual manner. Thus, the sensor/probe ports 101*b* may be used to visually monitor the status of the sensor/probe.

Integral with the bioreactor may be one portion of the mixing system. Specifically, as shown in FIG. 2, the portion of the mixing system included with the bioreactor may include one portion 208 of the mixing system—an impeller plate and impeller hub. The impeller plate connects to the drive system of the motor to power the impeller, and also provides a seal between the motor and the interior of the bioreactor.

Some embodiments of the invention provide one or more exceptional mixing systems, which provides the system with an inexpensive method for providing agitation to the contents of the bioreactor. Such mixing systems may utilize materials such as HDPE (high-density polyethelene) and/or other gamma-irradiatable, biocompatable plastics. One or more components of the mixing system may be manufactured by machining blocks of material, but may also be molded and/or cast.

Figure 3:
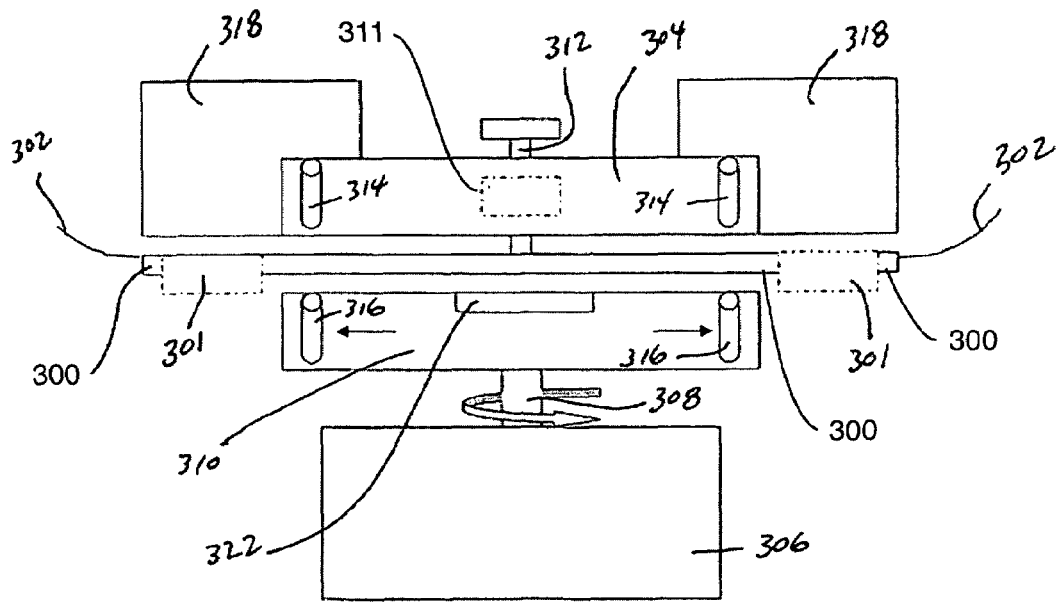
FIG. 3 is a schematic of a mixing system for a bioreactor system according to an embodiment of the present invention.

One such mixing embodiment is illustrated in FIG. 3. The mixing system according to this embodiment presents a magnetically driven impeller—thus, the motor is not directly connected to the impeller. Instead, magnets contained in a motor hub through magnetic attraction, drive magnets contained in an impeller hub. It is worth noting, that at least the motor portion (and other motor associated components), may be mounted on the support structure/tank/dolly.

As shown, the system generally includes an impeller plate 300 affixed to a side of the bioreactor wall 302, preferably at a lower portion thereof, an impeller hub 304, a motor 306, a motor shaft 308 and a motor hub 310. The impeller plate may be affixed to the wall of the bioreactor by heat welding together two halves of a two-piece impeller plate, and sandwiching the bioreactor wall therebetween or onto the wall. Alternatively, an opening in the wall of the bioreactor allows a central portion of the impeller plate to extend from an exterior of the bioreactor to the interior (or visa-versa). Then a sealing ring (not shown) could be adhered or the bioreactor heat welded directly to an outer circumference of the impeller plate to seal the bioreactor wall therebetween. Still one other alternative may be an undersized opening in the wall of the bioreactor which forms a seal with an circumferencial edge of the impeller plate which is slightly larger than the opening.

One important feature according to one embodiment of the invention is directed to the inclusion of one or more porous, micro-porous, or ultrafiltration elements 301 in the impeller plate. The element may be used to allow a gaseous sparge or fluids into and out of the bioreactor. Such sparging and/or fluid addition or removal may be used in conjunction with the mixing system (i.e., the rotation of the impeller hub). Sparging is the use of a mixing force (typically air) near the bottom of the reactor. The rising gas bubbles and the lower density of gas-saturated liquid rise, displacing gas-poor liquid which falls, providing top-to-bottom circulation. The path of rising liquid can be guided by means of dividers inside the chamber of the bag, or via baffles (see above). For example, such a bag may include a sheet of plastic bisecting the chamber of the bag vertically with a gap at the top and bottom. Gas may be added on one side only, of this divider, causing the gas and gas-rich liquid to rise on one side, cross over the top of the barrier, and descend on the other side, passing under the divider to return to the gas-addition point.

In some embodiments of the invention, a high shear zone beneath the rotating impeller affords increased performance features of the system. Used in combination with the porous materials (with macro, micron, submicron or nano pore size) described above, the shear zone may be used to perform a variety of purposes, gas sparging; fluid withdrawal from the vessel; solid/liquid or cell culture separations (e.g., any particulate separation in which solids are retained in the bioreactor and fluid filtrate is removed)—examples include semi- or continuous perfusion culture, cell separations, resin separation, etc.; and product or solute concentration or buffer exchange in the application that the porous element is in the ultrafiltration range.

In the embodiment illustrated in FIG. 3, the interior side of the impeller plate may include a post 312 to which a central opening in the impeller hub 304 receives. The impeller hub is preferably maintained a slight distance above the surface of the impeller plate to prevent friction therebetween. Low friction materials may be used in the manufacture of the impeller hub to minimize friction between the impeller hub and the post; alternatively, a bearing 311 may be included to reduce friction.

The impeller hub also preferably includes at least one magnet 314, and preferably more than one, which is preferably positioned at a periphery of the hub and preferably corresponding to a position of a magnet(s) 316 provided on the motor hub 310. The impeller hub also includes one or more and preferably a plurality of impeller blades 318. It is also worth noting that the embedded magnet(s) in the impeller can remove ferrous or magnetic particles from solutions, slurries or powders.

The motor hub 310 is generally centrally mounted on a shaft 308 of motor 306. In addition to the magnets 316, the motor hub may also include a lazy-susan bearing 322 so as to prevent friction between the motor hub and the impeller plate, although, alternatively (or in addition thereto), low friction materials may be used to reduce friction (e.g., low friction plastics).

The lazy-susan bearing also contributes to the minimization of the gap between the motor hub and the impeller plate. Although the thinnest impeller plate thickness is desired, it sometimes cannot be achieved. As tank scale increases, hydrostatic pressure on the inside of the tank and impeller plate increases, which may result in downward deflection/deformation of the impeller plate and central post. If deformation is not prevented, the impeller hub may bottom out on the impeller plate and create drag, thus reducing coupling forces and causing friction. This in turn may result in the shedding of particles into the contents of the bioreactor. Thus, the lazy-susan bearing mounted in the center of the motor hub may support the underside of the impeller plate to help aid in preventing deflection of the impeller plate from hydrostatic pressure. Accordingly, this feature ensures proper impeller operation in large scale applications and permits use of a very thin impeller plate thickness, while maximizing torque transmission.

Applicants of the present invention have found that the strength of the torque transmission from the motor hub to the impeller hub via the magnetic coupling may be determined by one or more of the following: the width of the gap between the two hubs, collectively comprises of the thickness of the impeller plate and the combined width of the two gaps between the impeller hub and the plate, and the motor hub and the plate; avoidance or elimination of any interfering ferrous or magnetic substances in the motor hub, impeller plate or the impeller hub (this is achieved in some embodiments of the present invention by manufacturing the one or more or all components of the mixing systems from plastic, for example); the number of magnets; the magnetic force of the magnets; the number of concentric rings of magnets; and the distance of magnets from the center of the hubs.

Accordingly, the gap between the two hubs is preferably adjustable between about 0.001 inch to 0.750 inch, and more preferably, between about 0.125" and about 0.500 inches. The number of magnets used may be one, but is preferably between about 2-50, and most preferably between about 3 and 10 magnets, with such magnets having a magnetic force of between about 1-100 million Gauss Oersted (MGOe), and most preferably between about 20-50 million MGOe. In one embodiment, the type of magnets which are used are a grade of neodymium magnet. Preferably the grade of neodymium is N38, which includes a maximum energy product of 38 MGOe. The number of concentric rings of magnets may range from 1-4, with the distance from the hub of the rings of magnets being between about 0.250 inches to about 16 inches, and most preferably between about 0.500 inches and 12 inches.

Figure 4:
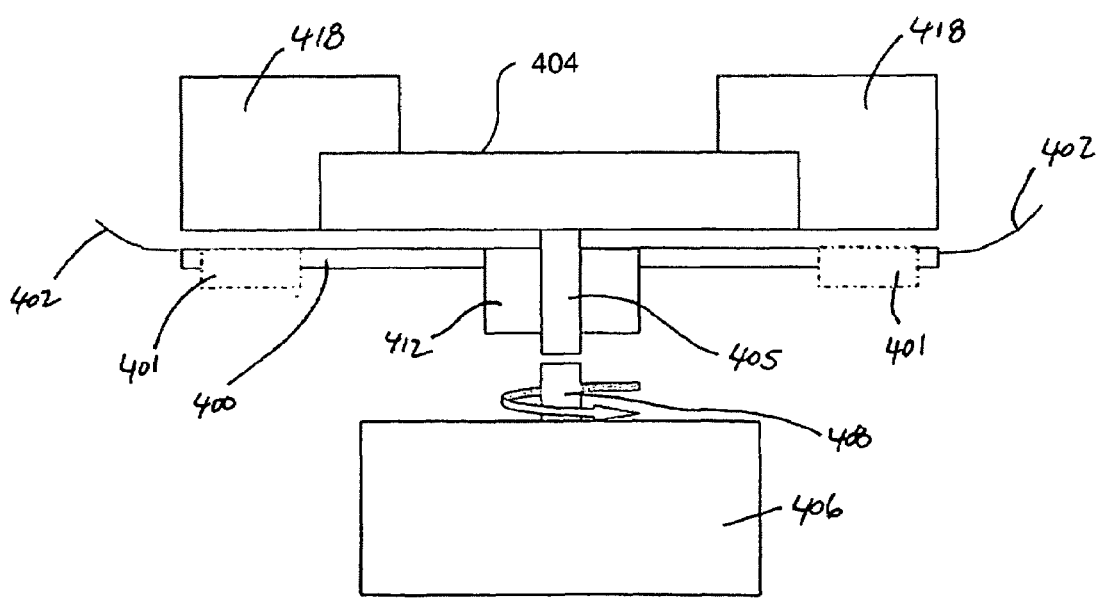
FIG. 4 is a schematic of a mixing system for a bioreactor system according to another embodiment of the present invention.

FIG. 4 illustrates an alternate embodiment to the mixing system, related to a mechanically driven impeller. As shown, this embodiment generally includes an impeller plate 400, an impeller hub 404 with shaft 405, an external motor 406 with shaft 408. The connection of shafts between the impeller hub shaft and the motor shaft may be accomplished in an manner familiar to one of ordinary skill in the art (e.g., gear box, hex drive, and the like).

The impeller plate is preferably affixed to a side of the bioreactor wall 402 at a lower portion thereof. The impeller plate may be affixed to the wall of the bioreactor by any of the methods recited for the embodiment of FIG. 3. The porous, micro-porous, or ultrafiltration elements 401 may also be included in the present embodiment to allow gaseous sparge or fluids into and out of the bioreactor.

In the embodiment illustrated in FIG. 4, the shaft of the impeller hub may be received in a seal 412 (which may also include a bearing) centrally located in the impeller plate. The seal insures that the contents of the bioreactor are not contaminated. The impeller hub is preferably maintained a slight distance above the surface of the impeller plate to prevent friction therebetween. The impeller hub also includes one or more and preferably a plurality of impeller blades 418.

Figure 7:
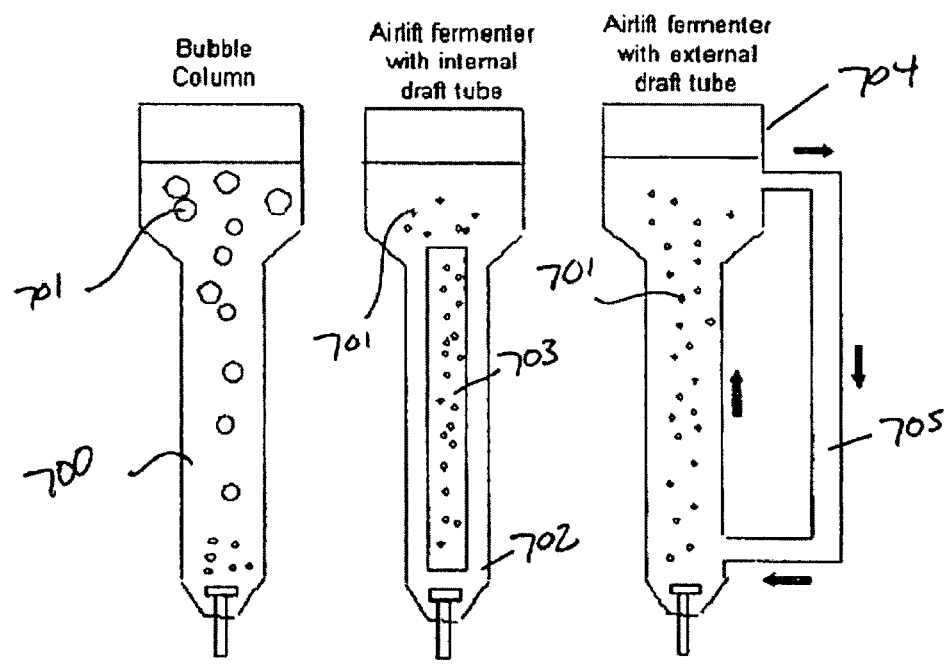
FIG. 7 is a diagram illustrating three concepts of a bubble column/air-lift mixer as applied to a disposable bioreactor according to an embodiment of the present invention.

In yet another embodiment (sees FIGS. 7 and 8B) a bubble column or airlift system (utilizing bubbles of air/gas 701) is used with the disposable bioreactor bag—which provides for a mixing force by the addition of gas (e.g., air) near the bottom of the reactor. Such embodiments may include a bubble column 700, an air-lift fermenter 702 with internal draft tube 703 and an air-lift fermenter 704 with external draft tube 705 (the direction of the bubbles may correspond to the direction of the arrows).

Accordingly, the rising gas bubble and the lower density of gas-saturated liquid rise, displacing gas-poor liquid which falls, providing top-to-bottom circulation. The path of rising liquid can be guided by means of dividers inside the chamber of the bag. For example, using a sheet of plastic which bisects the interior of the bioreactor bag, preferably vertically, with a gap at the top and the bottom. Gas may be added on one side of the divider, causing the gas and gas-rich liquid to rise on one side, cross over the top of the barrier sheet, and descend on the other side, passing under the divider to return to the gas-addition point. It is worth noting that the bubble column/air-lift mixing system and method may be combined with either impeller based mixing system described above.

Figure 5A:
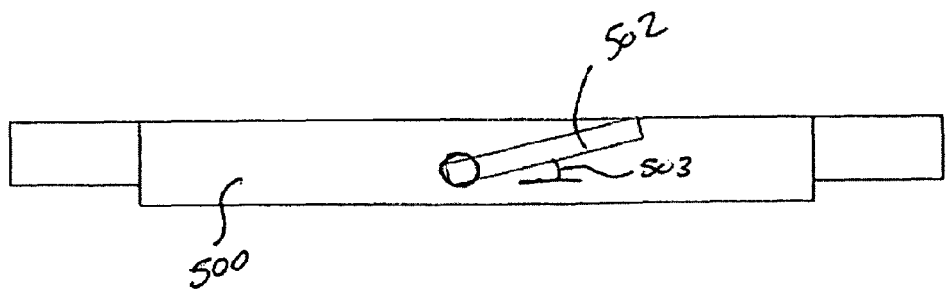
FIG. 5A is a side view of an impeller hub illustrating a position of a deformable impeller blade when the impeller hub is at rest, according to an embodiment of the invention.
Figure 5B:
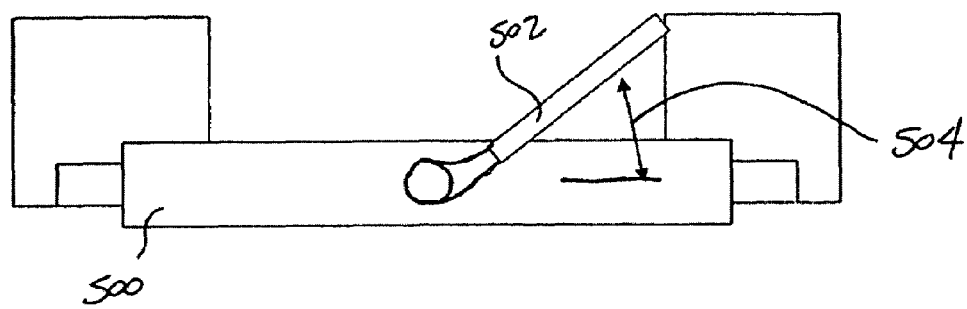
FIG. 5B is a side view of the impeller hub according to the embodiment illustrated in FIG. 5A, illustrating a position of the deformable impeller blade when the impeller hub is rotated at a particular speed.
Figure 6:
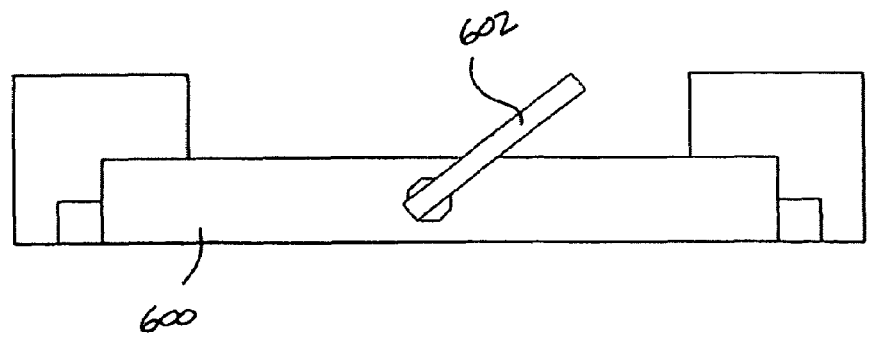
FIG. 6 is a side view of an impeller hub having a pivotable, fixed impeller blade(s), according to another embodiment of the present invention.

In either of the impeller-type mixing systems, further embodiments may be directed to variable-pitch impeller blades. As shown in FIGS. 5-6, the variable-pitch blade may comprise deformable blades or impeller blades which swivel. Specifically, as shown in FIG. 5A, an impeller hub 500 may include a deformable, variable-pitch blade 502, which is in a substantially reclined position when the impeller hub is stationary (or at a small angle 503 to the top and/or bottom surface of the impeller hub), and which is inclined at angle 504 to the top and/or bottom surface of the impeller hub when the impeller hub is rotated. The angle the blade forms with the impeller hub may depend upon the rotational velocity of the impeller hub; thus, the faster the impeller hub rotates, the more inclined the blade is to the top and/or bottom surface of the impeller hub. A material used in the manufacture of the impeller blades having flexible properties may be used (according to one embodiment) to provide the above-noted functionality. Such flexible materials (e.g., plastic, engineered plastic) are familiar to those of skill in the art.

In an alternative embodiment shown in FIG. 6, the pitch of the impeller blade 602 relative to the top and/or bottom surface of the impeller hub 600 may be obtained by manually rotating the blade relative to the impeller hub. This may be accomplished by manufacturing the impeller hub with respective openings to receive a pivoting shaft of each blade. The shaft may be slightly oversized relative to the size of the respective opening in the impeller hub. Alternatively, impeller hubs having a set, predetermined blade pitch may be manufactured and included with in a bioreactor. Thus, bioreactor bags having particular set-pitch impeller blades may be separately manufactured and available for a particular application.

The mixing systems described above allow the system to mix fluids or solids of any type. In particular, fluids inside the bioreactor may be mixed to provide distribution of nutrients and dissolved gasses for cell growth applications. The same disposable vessel may be used for mixing buffers and media or other solutions in which a disposable product contact surface is desirable. This may also include applications in which the vessel is not required to be sterile or maintain sterility. Moreover, the present system enables the tank holding the fluids/mixtures/gases to be removed and discarded such that the tank is not soiled by the fluids that are mixed in the bioreactor bag. Thus, the tank need not to be cleaned or sterilized after every use.

EXAMPLE

Mixing was tested with water with CHO (mammalian) cells expressing an antibody fusion protein at 150 L scale using an HDPE, magnetically driven impeller, with HDPE plate and shaft, for mixing and porous HDPE tubing for sparging. An optical patch for DO provided dissolved oxygen monitoring and feedback control of gas flow. Temperature was controlled by a thermocouple against the outer surface of the bag and on/off heating was provided by an electric blanket. In this test run, mammalian cells were grown to high density and maintained at high viability, demonstrating successful reduction to practice of this design for cell culture.

EXAMPLE 2

Inventory List for Disposable Bioreactor System

The following is a list of components for an exemplary bioreactor system having a disposable bioreactor bag according to an embodiment of the present invention (see also, FIG. 1B)

| Subassembly Component QTY Description/Options | | |
|---|---|---|
| Component | Quantity | Description |
| Tank Tank Shell | 1 | 316SS Tank shell with fitments |
| Tank Coil and Insulation | 1 | Heat transfer path wrapped around tank shell |
| Temperature controller Unit | 1 | Stand-alone TCU integrated to main skid controller |
| Tank jacket hoses | 1 | Connections between TCU and tank coil |
| Tank sight glass | 1 | Viewing window on tank shell side |
| Tubing manager | 1 | Panle with tubing grommets on top of tank |
| I&C pH probe & analyzer | 2 | |
| Dissolved Oxygen & Analyzer | 2 | |
| Load Cells | 3 | |
| Load Cell analyzer | 1 | |
| Thermocouple | 5 | |
| Flowmeter - Sparge | 1 | Rotameter to provide local visual indication of flow to sparge element(s) |
| Flowmeter - head sweep | 1 | Rotameter to provide local visual indication of gas flow to headspace |
| Flow switch - | 1 | Flow detector to indicate filter |

-continued

| Subassembly Component QTY Description/Options | | |
|---|---|---|
| Component | Quantity | Description |
| exhaust line | | flow or blockage |
| Mass flow controller - head sweep | 1 | |
| Mass flow controller - sparge | 4 | |
| Acid feed pump | 1 | Peristaltic pump - small |
| Base feed pump | 1 | Peristaltic pump - small |
| Antifom feed pump | 1 | Peristaltic pump - small |
| Media Feed Pump | 1 | Peristaltic pump |
| Discharge pump | 1 | Peristaltic pump |
| Agitator motor, reducer, drive head | 1 | Baldor ½ HP washdown duty or equivalent |
| Agitator controller | 1 | Baldor washdown duty or equivalent |
| Power Distribution | 1 | |
| I/O cabinet and switches | 1 | |
| PLC controller | 1 | |
| Operator Interface | 1 | |

Having now described a few embodiments of the invention, it should be apparent to those skilled in the art that the foregoing is merely illustrative and not limiting, having been presented by way of example only. Numerous modifications and other embodiments are within the scope of ordinary skill in the art and are contemplated as falling within the scope of the invention as defined by the appended claims and equivalents thereto.

We claim:

1. A bioreactor system comprising:
a disposable container for housing biomaterials for processing, the disposable container comprising a single chamber including at least one input port;
a fitting comprising a porous surface associated with the input port and configured for allowing the passage of an inlet gas stream and controlling gas bubble size and distribution prior to addition of the inlet gas stream to the interior of the single chamber, wherein the pore size of the porous surface is chosen from macro, micron, submicron, nano, and combinations thereof;
a disposable mixing system comprising an impeller positioned above the porous surface and within the single chamber at a lower portion of the single chamber, the impeller configured to be driven by a motor magnetically coupled to the impeller and external to the lower portion of the single chamber such that biomaterials contained within the single chamber are mixed and gas bubble circulation is increased;
at least one exhaust port;
at least one harvest port;
a structure for supporting the disposable container;
one or more sensors for sensing one or more parameters of the biomaterials in the container; and
a heater for heating the contents of the disposable container, the heater having a thermostat.

2. The bioreactor system of claim 1, wherein the disposable container comprises a plastic container or a flexible plastic bag.

3. The bioreactor system of claim 1, wherein the single chamber includes at least one baffle configured for restricting circular flow or preventing vortexing.

4. The bioreactor system of claim 1, wherein the disposable mixing system comprises a bubble column in conjunction with a partial divider positioned in the interior of the single chamber.

5. The bioreactor system of claim 1, wherein the porous surface is arranged to allow one or two-way fluid communication between an interior of the single chamber and an exterior of the single chamber.

6. The bioreactor system of claim 1, wherein the heater comprises an area of material positioned on the exterior of the disposable container.

7. The bioreactor system of claim 1, wherein the heater comprises a blanket of material or metal jacket containing heated or cooled water wrapped around at least a portion of the exterior of the disposable container.

8. The bioreactor system of claim 7, wherein the heater is positioned within the disposable container or on the exterior of the disposable container.

9. The bioreactor system of claim 1, wherein the one or more sensors comprise sensors for detecting at least one of dissolved oxygen dissolved carbon dioxide, mixing rate, gas flow rate, temperature, pH and pressure.

10. The bioreactor system of claim 1, further comprising a computer for controlling the bioreactor system.

11. The bioreactor system of claim 1, further comprising at least one of an air supply, a carbon dioxide supply, and an oxygen supply.

12. The bioreactor system of claim 1, further comprising transporting means for moving the support structure.

13. The bioreactor system of claim 12, wherein the transporting means comprises a dolly.

14. A bioreactor system comprising:
a support structure;
    a disposable container comprising a single chamber positioned within the support structure, the disposable container including:
    an impeller plate affixed to a lower portion of the single chamber, the impeller plate including a post having an end projecting into the single chamber;
    a fitting attached to the impeller plate, the fitting comprising a porous surface arranged to allow one or two-way fluid communication between an interior of the single chamber and an exterior of the single chamber, the porous surface having a pore size chosen from macro, micron, submicron, nano, and combinations thereof;
    a disposable impeller hub mounted on the post, the disposable impeller hub having at least one disposable impeller blade and having at least one magnet, the at least one impeller blade positioned above the porous surface and arranged on the post;
    a motor having a shaft, the motor being provided adjacent to or within the support structure; and
    a motor hub mounted on the motor shaft, the motor hub including at least one magnet, wherein upon mounting of the disposable container comprising a single chamber within the support structure, the motor hub aligns with the impeller plate such that the magnet of the motor hub may align with the magnet of the disposable impeller hub to drive the disposable impeller hub when the motor shaft rotates.

15. The bioreactor system of claim 14, wherein the motor hub further includes a lazy-susan bearing, wherein the bearing is positioned within the hub such that a portion of the bearing contacts one side of the impeller plate.

16. The bioreactor system of claim 14, wherein the pore size of the porous surface is from about 2 microns to about 10 millimeters.

17. The bioreactor system of claim 14, wherein the fluid communication is configured for introducing a gas sparge to the interior of the disposable container or for removing fluids from the interior of the disposable container.

18. The bioreactor system of claim 14, wherein the at least one disposable impeller blade comprises a variable pitch impeller blade.

19. The bioreactor system of claim 18, wherein the pitch of the disposable impeller blade changes depending upon the rotational speed of the impeller hub.

20. The bioreactor system of claim 18, wherein the pitch of the disposable impeller blade is manually adjusted.

21. The bioreactor system of claim 1, wherein the pore size of the porous surface is from about 2 microns to about 10 millimeters.

22. The bioreactor system of claim 21, wherein the pore size of the porous surface is from about 5 microns to about 3 millimeters.

23. The bioreactor system of claim 1, wherein the porous surface associated with the input port and configured for allowing the passage of an inlet gas stream and controlling gas bubble size and distribution prior to addition of the inlet gas stream to the interior of the single chamber is also adapted for use as a particulate separation device.

24. The bioreactor system of claim 1, wherein all surfaces configured for contact with the biomaterials housed for processing are disposable.

25. The bioreactor system of claim 14, wherein the porous surface arranged to allow one or two-way fluid communication between an interior of the single chamber and an exterior of the single chamber, is also adapted for use as a particulate separation device.

26. The bioreactor system of claim 14, wherein the disposable impeller hub and the motor hub each include at least two magnets.

27. The bioreactor system of claim 16, wherein the pore size of the porous surface is from about 5 microns to about 3 millimeters.

* * * * *